(12) United States Patent
Kjellstrand (10) Patent No.: US 6,663,829 B1
(45) Date of Patent: Dec. 16, 2003

(54) METHOD AND APPARATUS FOR REDUCING THE DEGRADATION OF HEAT SENSITIVE COMPONENTS IN MEDICAL SUBSTANCES DURING HEAT STERILIZATION

(75) Inventor: Per Kjellstrand, Södra Sandby (SE)

(73) Assignee: Gambro AB (SE)

( * ) Notice: Subject to any disclaimer, the term of this patent is extended or adjusted under 35 U.S.C. 154(b) by 0 days.

(21) Appl. No.: 09/807,036

(22) PCT Filed: Oct. 20, 1999

(86) PCT No.: PCT/SE99/01889

§ 371 (c)(1),
(2), (4) Date: Apr. 5, 2001

(87) PCT Pub. No.: WO00/24433

PCT Pub. Date: May 4, 2000

(30) Foreign Application Priority Data

Oct. 23, 1998 (SE) .............................................. 9803627

(51) Int. Cl.$^7$ ................................................ A61L 2/00
(52) U.S. Cl. ...................... 422/1; 422/25; 422/40; 422/41; 422/307; 422/308; 604/28; 604/29; 604/408; 604/409; 604/410; 206/219; 206/568; 206/570
(58) Field of Search .................. 422/1, 25, 40, 422/41, 256, 307, 308; 604/28, 29, 408, 410, 409; 206/219, 568, 570

(56) References Cited

U.S. PATENT DOCUMENTS

| | | | | |
|---|---|---|---|---|
| 4,994,057 A | * | 2/1991 | Carmen et al. | 604/416 |
| 4,997,083 A | * | 3/1991 | Loretti et al. | 206/219 |
| 5,536,469 A | * | 7/1996 | Jonsson et al. | 422/1 |
| 6,241,943 B1 | * | 6/2001 | Wieslander et al. | 422/1 |

FOREIGN PATENT DOCUMENTS

| | | |
|---|---|---|
| DE | 43 21 999 C1 | 10/1994 |
| WO | 93/09820 A1 | 5/1993 |
| WO | 97/05852 A1 | 2/1997 |

* cited by examiner

Primary Examiner—Krisanne Thornton
(74) Attorney, Agent, or Firm—Lerner, David, Littenberg, Krumholz & Mentlik, LLP (57) ABSTRACT

Methods and apparatus are disclosed for reducing the degradation of heat sensitive components contained in a medical substance during heat sterilization of a heat sterilizable container including a first chamber including a first amount of a first medical substance and a second chamber including a second amount of a second medical substance, the first amount being greater than the second amount. The method includes heating the heat sterilizable container to a first predetermined temperature for sterilizing the first and second medical substances, thermally insulating the second chamber during at least a portion of the heating of the heat sterilizable container to the first predetermined temperature, holding the heat sterilizable container at the first predetermined temperature for a first predetermined time period, and cooling the heat sterilizable container thereafter.

22 Claims, 4 Drawing Sheets

METHOD AND APPARATUS FOR REDUCING THE DEGRADATION OF HEAT SENSITIVE COMPONENTS IN MEDICAL SUBSTANCES DURING HEAT STERILIZATION

The present invention concerns a method and an apparatus for reducing the degradation of heat sensitive components in medical substances during heat sterilisation, wherein the medical substances are contained in a multiple chamber recipient that comprises a first chamber with a first medical substance and at least one second chamber with an amount of a second medical substance that is smaller than that of the first medical substance, and the multiple chamber recipient is heated to a predetermined temperature for sterilising the medical substances, is held at this temperature for a predetermined time period and is subsequently cooled.

The method can, for example, be utilised with multiple chamber recipients with medical substances for parenteral feeding/nutrition, however the method is in particular to be used with multiple chamber recipients that contain medical substances for generating a dialysis fluid for peritoneal dialysis.

TECHNICAL BACKGROUND

Currently, haemodialysis is mainly used for acute kidney failure while for chronic kidney failure, besides transplantation, haemodialysis and peritoneal dialysis are utilised. In the case of peritoneal dialysis, the abdominal cavity is repeatedly filled at intervals with a dialysis fluid that is then removed after a hold time. The dialysis fluid is generally a buffered ionic solution with an osmotic means, wherein currently glucose is mainly used as an osmotic means and lactate is mainly used as a buffer. In this way, urea and other substances normally removed from the kidneys and excess water can be removed from the body. These dialysis fluids are produced in factories, transferred to plastic bags of two to five liter capacity and sterilised, in a similar manner to solutions for parenteral nutrition.

A disadvantage of these dialysis fluids is the presence of degradation products. At present, it is assumed that during heat sterilisation these degradation products and the accompanying brownish colour of the fluid are produced by the glucose. It is further presumed that some of these degradation products are responsible for bioincompatability reactions generated by the dialysis fluid. Studies confirm that the degradation products react strongly with biological tissue and have a substantial effect on the immune system and the cells of the peritoneum, either alone or in combination with lactate and/or a low pH value.

Theoretically, the dialysis fluids could be rendered sterile by filtration in place of the heat sterilisation. In practice, however, this is not possible because essentially all countries stipulate that medical solutions must be sterilised by heat.

However, it is known that the degradation of glucose can be markedly reduced when the sterilisation temperature is increased and simultaneously the sterilisation time shortened. It is likewise known that the glucose degradation depends strongly on the pH value, and for example is at its lowest with a pH value between 3.0 and 3.5. However, a peritoneal dialysis fluid with such a low pH value is not permitted for the treatment of patients, for this a pH value of a little over 7 would be optimal, for example 7.1 to 7.4. As a compromise, therefore, a pH value of about 5.3 is set for conventional dialysis fluids. However, from a medical point of view, this is still too low and is probably the cause of infusion pain in some patients. Furthermore substantial amounts of degradation products are still generated during heat sterilisation, which is undesirable for the reasons already mentioned.

An improvement is proposed in WO 93/09820. In the dialysis fluid disclosed here, the glucose is isolated in a small separate second chamber from the rest of the dialysis fluid located in a first chamber. The glucose is separated in this second chamber with a high concentration and a low pH value, so that the formation of degradation products of glucose during heat sterilisation is substantially reduced. The pH value of the glucose in the separate second chamber is about 3.2, while the remainder of the solution in the larger chamber has a pH value of around 7. After mixing the glucose with the rest of the solution the mixture has a pH value of around 6.4, which offers an additional advantage in terms of tolerance by patients.

In WO 97/05852 a further development of this dialysis fluid is known in which the glucose is separated into two separate chambers, namely a second and third chamber, each with different concentrations. The concentrations are selected such that upon mixing the glucose from the second chamber with the rest of the solution in the first chamber, a dialysis fluid with a glucose concentration of 1.5% is obtained, upon mixing the clucose from the third chamber with the rest of the solution in the first chamber a glucose concentration of 2.5% is obtained, and upon mixing the glucose in the second and third chambers with the rest of the solution in the first chamber a glucose concentration of 4% is obtained. In this way, the three most useful glucose concentrations can be made available with one dialysis fluid recipient, which offers a great advantage in terms of logistics and storage. In addition, this dialysis fluid contains low amounts of degradation products as a result of the low pH values in the second and third chambers.

Although this already represents a clear reduction in the amount of degradation products in the dialysis fluid, there is still a significant amount of degradation products present owing to the high glucose concentration. As a result of the small quantities in the second and third chambers compared to that of the remaining solution in the first chamber, the glucose concentrations in these second and third chambers will be heated much faster during the heat sterilisation than the rest of the solution in the first chamber, which contains the remaining components. This leads to the glucose in the second and third chambers being held for an unnecessary long period at the sterilisation temperature, which results in the unnecessary increase in degradation products. Consequently, while a considerable reduction in degradation products is achieved compared to conventional dialysis fluids, the quantity of degradation products present is nevertheless still unnecessarily high.

Finally, it is also possible to reduce the formation of degradation products during heat sterilisation of multiple chamber recipients by means of a two step heating procedure. In this, the heating of the multiple chamber recipient in the autoclave is interrupted at a predetermined temperature, so that the temperatures in the first and second, and possibly the third, chamber can become essentially equal. Subsequently, the heating of the multiple chamber recipient proceeds to the predetermined sterilisation temperature. However, it is difficult with this procedure to find the exact intermediate temperature at which no, or only few, degradation products will be formed during the hold period.

DESCRIPTION OF THE INVENTION

In view of this background it is thus an object of the present invention to provide a method, whereby the degradation of heat sensitive components in medical substances during heat sterilisation is reduced, wherein the medical substances are contained in a multiple chamber recipient having a first chamber with a first medical substance and at least a second chamber with an amount of a second medical substance that is smaller relative to the first medical substance, and the multiple chamber recipient is heated to a predetermined temperature to sterilise the medical substances, is held at this temperature for a predetermined time and is subsequently cooled.

This object is achieved in that the second chamber with the second medical substance is thermally insulated during the heating of the multiple chamber recipient.

In this way, a method is provided that reduces the degradation of heat sensitive components in the second chamber during the heat sterilisation of multiple chamber recipients with different substances. The end product after mixing the contents of the chamber thus likewise contains substantially lower amounts of degradation products.

The second chamber can contain a quantity of a medical substance that is low relative to that in the first chamber. If this substance contains components that form degradation products when held for a long period at the sterilisation temperature, it will be prevented that they are heated faster and consequently remain at the sterilisation temperature longer than the substance in the first chamber. However, it is also possible that the second chamber contains the same amount of a medical substance as the first chamber, but with some of the components of this substance being very heat sensitive, so that they may be subjected to the sterilisation temperature only for a shorter period of time relative to the substance in the first chamber. By means of the thermal insulation of the second chamber, the heating of the second chamber can also be deliberately delayed, as a result of which the desired hold time at the sterilisation temperature can be set.

The hold time of the second chamber at the sterilisation temperature can advantageously be more precisely adjusted, in accordance with a preferred embodiment, when the thermal insulation is removed at a predetermined time after commencing the heating of the multiple chamber recipient. In this way the point in time at which the second chamber of the multiple chamber recipient is also exposed to the heating environment can be accurately set. Furthermore, since the point in time of the cooling of the multiple chamber recipient is also predetermined, a precisely controlled heat sterilisation with a defined hold time at the sterilisation temperature is also separately possible for the second chamber.

In accordance with a further preferred embodiment, the time for removing the thermal insulation is advantageously determined such that the first and second medical substances in the first and second chambers have essentially the same F value at the end of the hold time. F is utilised here as a gauge of the capacity of a sterilisation process to kill microbes, or the sterilisation capacity of a sterilisation process, and is predominantly utilised in the food industry and in medicine. It is a reference gauge and signifies a specific rate of microbes killed during a sterilisation process, F representing the time required to achieve this specific death rate at 121° C.

If the first and second medical substances have essentially the same F value, then this indicates that both substances have undergone essentially the same degree of sterilisation and, in particular, that the second chamber or the second substance has not been subjected to an unnecessary oversterilisation as a result of overheating. Overheating the second chamber would lead to a substantial increase in the degradation products. It is to be noted at this point that a correlation exists between the F value and the degradation in the sense that with an increasing F value, the degradation products also increase, and vice versa.

In order to achieve an adequate sterilisation of the multiple chamber recipient, the latter is advantageously heated to a temperature of between 100° C. and 135° C., preferably to a temperature of 121° C. The sterilisation process is advantageously controlled such that the multiple chamber recipient is held for between 1 minute to several hours at this predetermined temperature, and preferably 15 minutes.

The method for reducing the degradation of heat sensitive components in medical substances described here is not limited only to multiple chamber recipients with two chambers, but may also be applied to multiple chamber recipients with more than two chambers. Therefore, according to another preferred embodiment, the method is utilised for a multiple chamber recipient that additionally includes a third chamber with an amount of a third medical substance that is smaller relative to that of the first medical substance, the third chamber being thermally insulated together with the second chamber during heating of the multiple chamber recipient. Here also the second chamber with the second medical substance and the third chamber with the third medical substance are advantageously arranged in a thermally insulating jacket, that is opened a predetermined time after commencing heating of the multiple chamber recipient. The second chamber and the third chamber can contain different amounts of the same substance or also the same amount of different substances.

The time at which the thermal insulation is removed is likewise advantageously defined such that the first and second and third medical substances in the first and second and third chambers have essentially the same F value at the end of the hold time. If the second and third chambers contain different amounts of a medical substance, the F value of the largest amount is determinate for the removal of the thermal insulation. This should be essentially the same as the F value in the first chamber. The F value of the smaller amount in the other chamber will then be somewhat higher; this deviation from the desired F value has to be accepted in view of the required sterilisation of the larger amount. However, in order to achieve a nearly equivalent F value in this case also, the insulation can be formed differently in areas. For example, it could be formed thinner in the area of the second or third chamber, when these contain a larger amount, so that the sterilising heat reaches the large amount before the removal of the insulation and is able to heat this a little. Or, the second and third chambers will be respectively insulated such that the insulation of each can be successively removed independently of one another.

The thermally insulating jacket may take any desired form. For example, it can consist of an insulating material which, upon reaching a predetermined temperature will collapse or shrink, thus allowing the elevated surrounding temperature to reach the multiple chamber recipient. In this way the heating of the second and possibly also the third chamber will be delayed, and as a result, the time during which the second and possibly the third chamber are held at the sterilisation temperature can be controlled.

Another possibility for a thermally insulating jacket is a container with thermally insulating walls. The second and possibly the third chamber would be laid in this container with the first chamber remaining outside, and the container would be closed. In this manner, the second and possibly the third chamber will be thermally insulated, so that initially only the first chamber is heated. When the predetermined point in time is reached, the container is opened and the second chamber and possibly third chamber will be exposed to the sterilising heat and heated to the same temperature as the first chamber. In this way, the hold time of the second and possibly third chambers can be precisely determined independently of that of the first chamber. When the predetermined hold time of the first chamber is terminated, the multiple chamber recipient is cooled down. During this, care should be taken that the cooling occurs rapidly, so that degradation products are not formed unnecessarily as a result of slow cooling.

The method can be applied to multiple chamber recipients of any desired form, however it is advantageously utilised with a multiple chamber recipient formed as a flexible bag. The method can likewise be applied to multiple chamber recipients that hold any desired medical substance. For example, the multiple chamber recipient may hold substances for parenteral feeding. Also, the substances can take any desired form. For example, the medical substances can be solutions in liquid form, they can also be concentrates in powder form. However, the method is preferably applied to multiple chamber bags containing medical substances for the production of a dialysis fluid for peritoneal dialysis. According to a preferred embodiment, the second medical substance and third medical substance in the second and third chambers, respectively, comprise different concentrations of glucose, that is required for the dialysis fluid, or, according to another preferred embodiment, the same concentration of glucose in different quantities.

DESCRIPTION OF THE DRAWINGS

Figure 1:
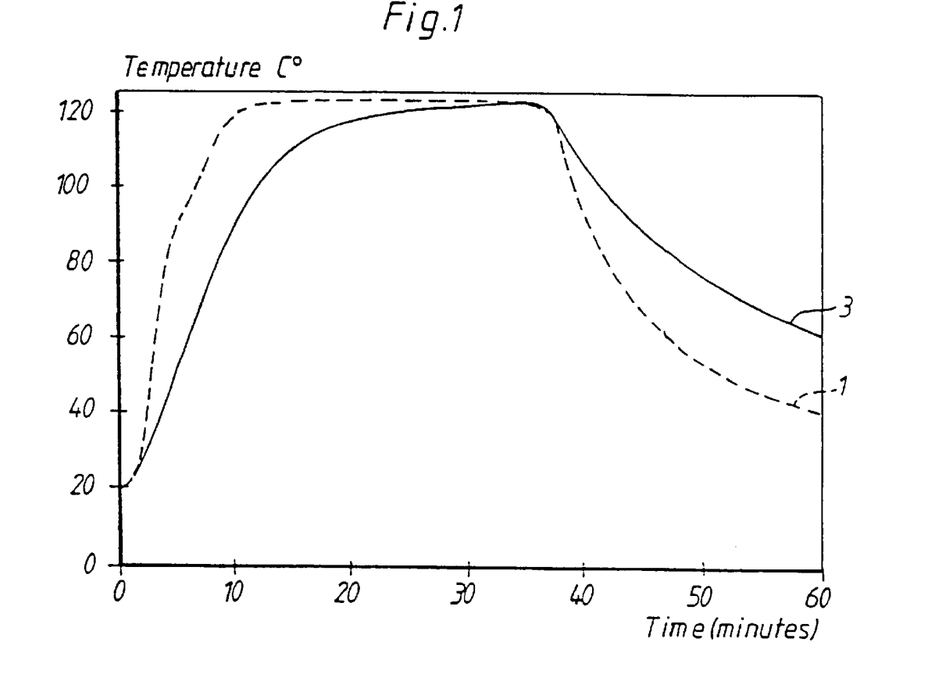
FIG. 1 is a graphical representation of the temperature curve in ° C. over time in minutes during the conventional heat sterilization of a double chamber bag.
Figure 2:
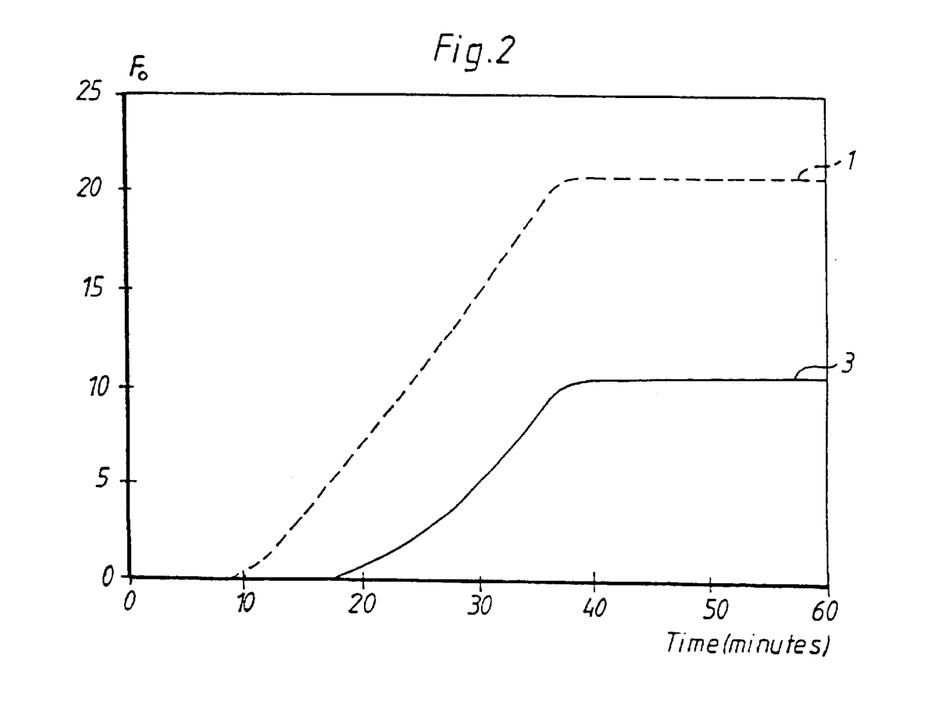
FIG. 2 is a graphical representation of the $F_o$, value over time in minutes during the heat sterilization according to FIG. 1.
Figure 3:
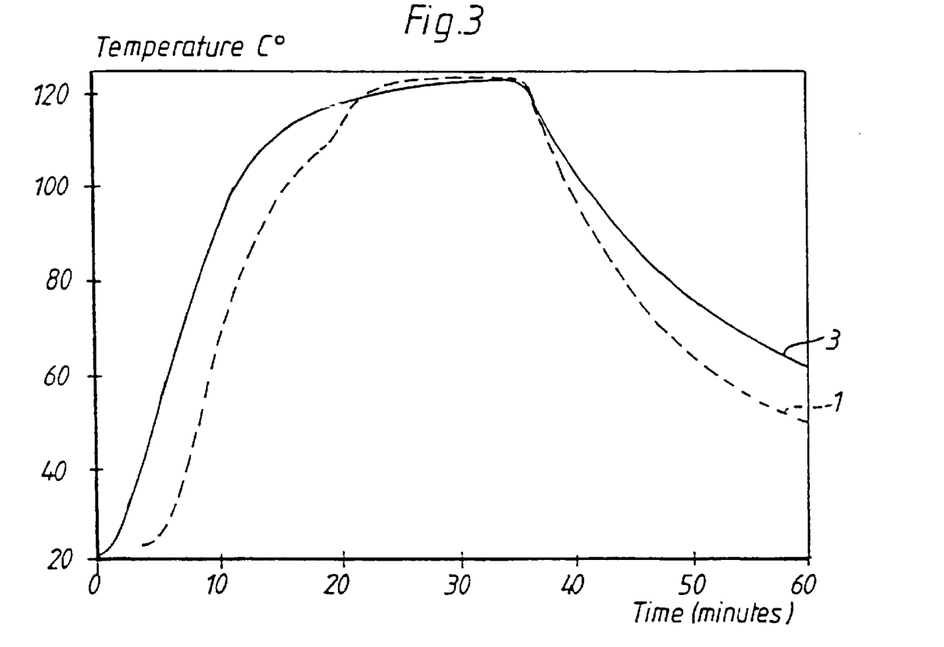
FIG. 3 is a graphical representation of the temperature curve in ° C. over time in minutes during the heat sterilization of a double chamber bag according to the method of the present invention.
Figure 4:
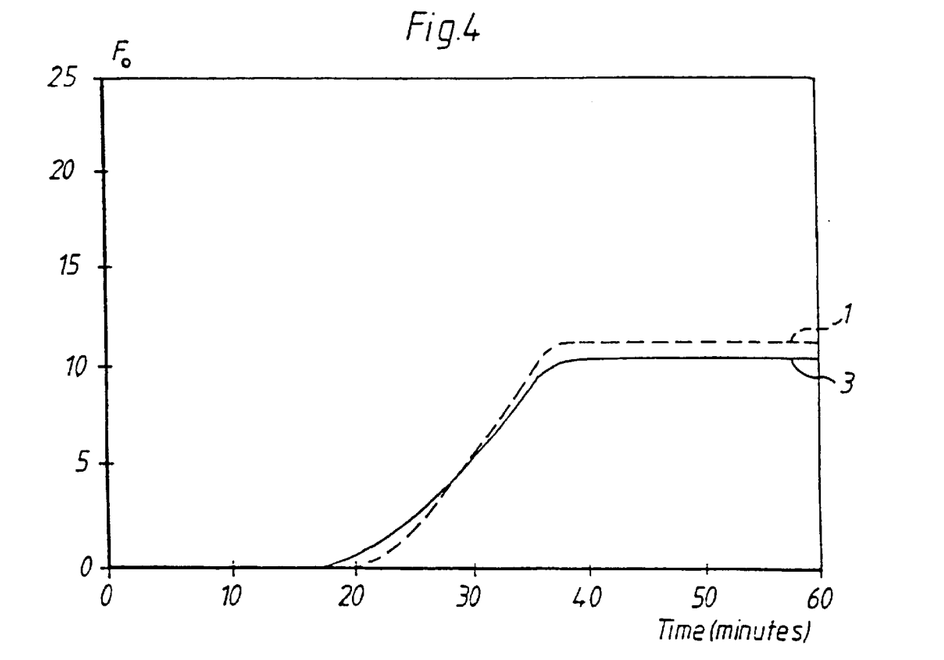
FIG. 4 is a graphical representation of the $F_o$ value over the time in minutes during the heat sterilization of FIG. 3.
Figure 5:
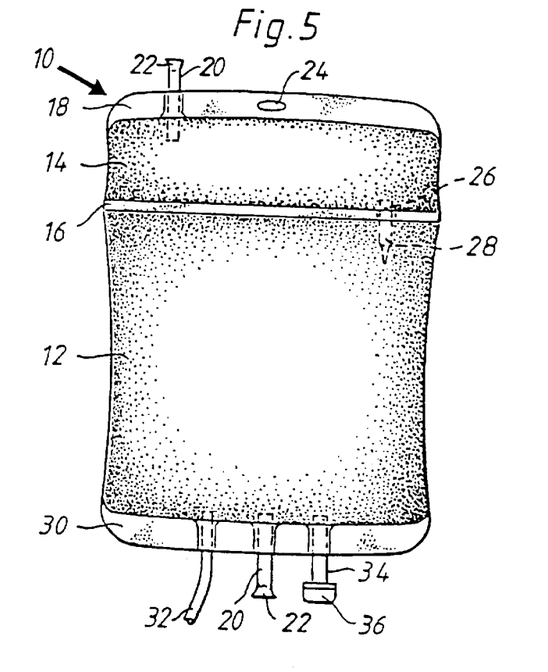
FIG. 5 is a side, elevational view of a double chamber bag for use in connection with the present invention.
Figure 6:
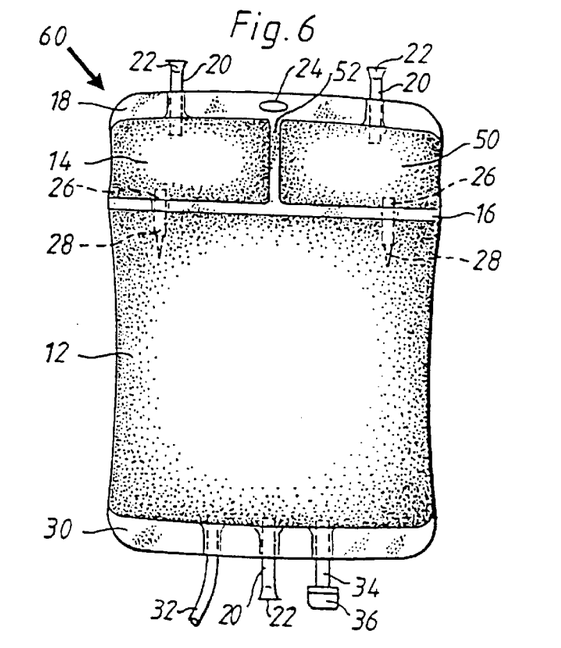
FIG. 6 is a side, elevational view of a triple chamber bag for use in connection with the present invention.
Figure 7:
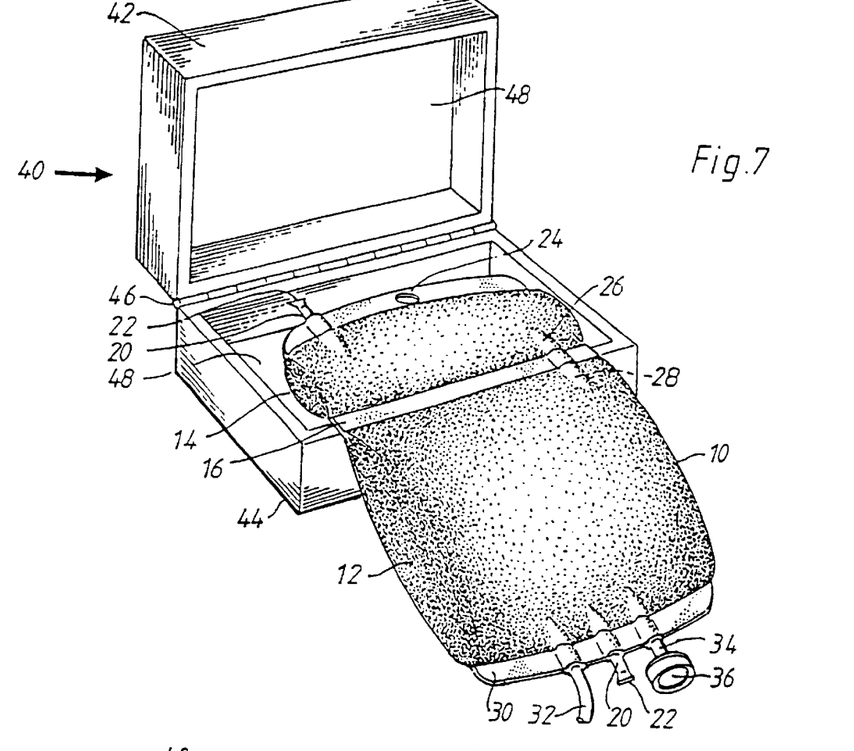
FIG. 7 is a front, perspective view of an apparatus for carrying out the method according to the present invention.

Examples for the method according to the invention are given by way of illustration in the accompanying drawings. The figures contained therein show the temperature curve and the F curve and thus the degradation, on the one hand, for the sterilisation of a double chamber bag according to conventional heat sterilisation in an autoclave, and on the other hand, for the heat sterilisation of a double chamber bag in an autoclave with the method according to the invention. Therein, the F value "$F_o$" is the F value corresponding to a sterilisation temperature of 121° C. There is shown in FIG. 1 the temperature curve in °C. over time in minutes during the conventional heat sterilisation of a double chamber bag;

FIG. 2 the $F_o$ value over time in minutes during the heat sterilisation according to FIG. 1;

FIG. 3 the temperature curve in ° C. over time in minutes during the heat sterilisation of a double chamber bag according to the method of the invention;

FIG. 4 the $F_o$ value over the time in minutes during the heat sterilisation of FIG. 3;

FIG. 5 a double chamber bag;

FIG. 6 a triple chamber bag;

FIG. 7 an apparatus for carrying out the method according to the invention; and

Figure 8:
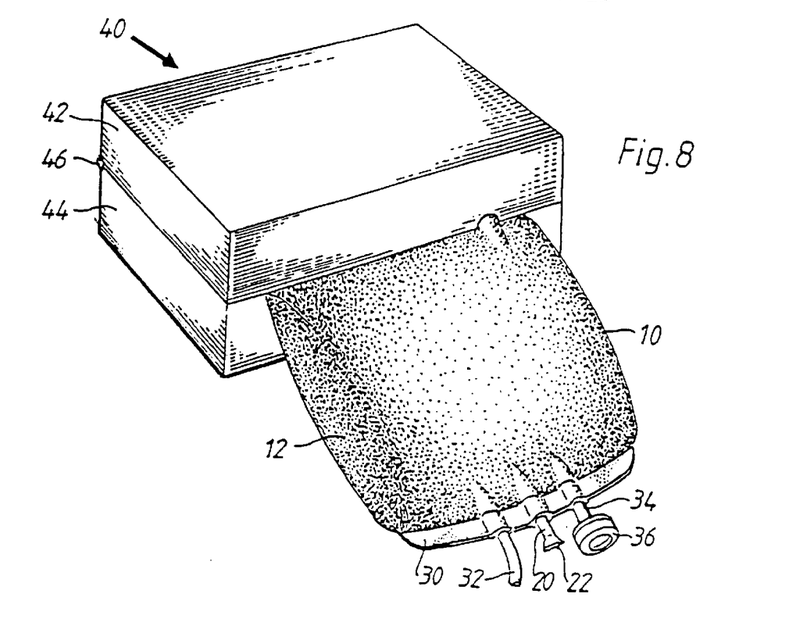
FIG. 8 is a front, perspective view of the apparatus of FIG. 7, in a closed state.

FIG. 8 the apparatus of FIG. 7 in a closed state.

DESCRIPTION OF PREFERRED EMBODIMENTS

In FIG. 1 there is shown the temperature curve of a double chamber bag during a conventional heat sterilisation in an autoclave, wherein the dashed line 1 shows the temperature curve in the second chamber, and the continuous line 3 shows the temperature curve in the first chamber. The second chamber contains a smaller quantity of medical substance compared to the first chamber. Therefore, the contents of the second chamber will be heated faster during heating of the multiple chamber bag, as can be clearly seen from the temperature curve (line 1) in the second chamber during the first ten minutes. The second chamber reaches the sterilisation temperature, which here is about 121° C., much faster, and is also held there substantially longer than the first chamber. The first chamber needs a longer period for heating owing to the larger quantity of medical substance, as is evident from the temperature curve (line 3) during the first ten minutes. The first chamber reaches the sterilisation temperature much later and is also held at this sterilisation temperature for a shorter period (line 3). After reaching the end of the predetermined hold time at the sterilisation temperature for the multiple chamber recipient or for the first chamber, the multiple chamber recipient is cooled down. During this, the second chamber, or the contents of the second chamber, cools faster (line 1) owing to the smaller quantity of medical substance relative to that of the first chamber (line 3). The longer hold time of the second chamber at the sterilisation temperature causes a higher formation of degradation products and also leads to an elevated F value in the second chamber, which is superfluous in terms of sterilisation.

This is shown in FIG. 2. FIG. 2 shows the $F_o$ curve during the heat sterilisation according to FIG. 1. As can be clearly seen here, in the second chamber (line 1) an $F_0$ value is obtained that is almost double that in chamber 1 (line 3). The $F_o$ value of about ten obtained in chamber 1 is a normally sought and sufficient $F_o$ value for sterilisation, while the $F_o$ value obtained in the second chamber of around twenty is unnecessarily high.

To avoid this over-sterilisation and the accompanying increased degradation of, for example, glucose contained in the second chamber, the second chamber is provided with a thermally insulating jacket, that is removed a predetermined time after the beginning of the heating process. The resulting temperature curve during heat sterilisation is shown in FIG. 3. Here it can be seen clearly that the beginning of the heating of the second chamber (line 2) is markedly delayed compared to the beginning of the heating of the first chamber (line 3). After about twenty minutes, the thermally insulating jacket of the second chamber is removed, so that the second chamber is likewise heated rapidly to the sterilisation temperature, together with the first chamber. After a predetermined hold time of the multiple chamber recipient at the sterilisation temperature, the multiple chamber recipient is cooled, as is apparent from the continuing temperature curve of the first and second chambers (line 3, line 1).

In contrast to the heat sterilisation of the multiple chamber recipient without the thermal insulation of the second chamber according to FIG. 1, the second chamber here remains held at the sterilisation temperature essentially as long as the first chamber. In this way, on the one hand, the excessive and unnecessary formation of degradation products is prevented and, on the other, an over-sterilisation of the medical substance contained in the second chamber is avoided.

This is shown in FIG. 4. FIG. 4 shows the $F_o$ curve during the heat sterilisation according to FIG. 3. Because the first and second chambers, or their contents, are held for essentially the same time at the sterilisation temperature, the result is an almost identical $F_o$ value. The $F_o$ value of the medical substance in the second chamber (line 1) differs only slightly from the $F_o$ value of the substance in the first chamber (line 3). Due to the later commencement of heating and the slightly higher temperature relative to that of the first chamber during the hold time, the $F_o$ temperature curve of the second chamber (line 1) lies slightly below the $F_o$ temperature curve of the first chamber (line 3) at the beginning, but then lies slightly above it at the end of the sterilisation. However an over-sterilisation of the second chamber has not occurred, nor were excessive degradation products formed in the second chamber during the sterilisation.

The method performed here by way of example on a two chamber bag can also be applied to three or multiple chamber bags, as described in detail above. In this case, the larger first chamber, or the first chamber filled with the larger amount of medical substance, determines the hold time of the multiple chamber bag in the autoclave, while the chamber of the second, and possibly third, fourth, etc. chambers provided with a thermally insulating jacket that includes the largest amount of medical substance, determines the time of removal of the thermally insulating jacket. The desired, lowest required F value, that corresponds to an adequate sterilisation, is always to be selected as a gauge for the hold time of the multiple chamber recipient in the autoclave or for the removal of the thermal insulation.

In FIG. 5 a double chamber bag 10 is shown, that is to be sterilised according to the method of the invention. The multiple chamber bag 10 includes a first larger chamber 12 and a second smaller chamber 14. In the present case, the multiple chamber recipient 10 contains a dialysis solution for peritoneal dialysis and includes an electrolytic solution in the first chamber 12 and a glucose solution in the second chamber 14.

The first chamber 12 is separated from the second chamber 14 by a welded seam 16, in which there is arranged a connecting tube 26. The connecting tube 26 is closed at one end by a break-off seal 28. A fill tube 20, through which the second chamber 14 is filled, is connected at the upper edge 18 of the multiple chamber recipient 10. The outer end of the fill tube 20 is provided with a seal 22 which may be achieved simply by melting the end of the fill tube 20 for example. Moreover, at the upper edge 18 there is provided an opening 24, by which the multiple recipient bag 10 can be suspended. At the lower edge 30 of the multiple chamber recipient 10, there is arranged a connection tube 32, by means of which the contents of the first chamber 12 can be supplied to a patient, who is not shown. Furthermore, there is also provided a fill tube 20 at the lower edge 30, through which the first chamber 12 is filled. This fill tube 20 is also provided with a seal 22 at its outer end. Finally, a feed tube 34 is also arranged at the lower edge 30, by means of which medication can be supplied to the contents of the first chamber 12, for example. The feed tube 34 is closed at its outer end with a septum 36, so that the injection of medication into the first chamber 12 is possible. Before the dialysis solution is administered to the patient, the contents of the first chamber 12 and second chamber 14 are mixed together. To this end, the break-off seal 28 is broken off so that the connecting tube 26 between the first chamber 12 and the second chamber 14 is opened. The contents of the second chamber 14 then run through the connecting tube 26 into the first chamber 12, and mix with the solution located therein. Subsequently, the mixed solution can be supplied to the patient through the connecting tube 32.

It is again to be noted at this point that the multiple chamber recipient 10 can also include a third, or even more chambers, the contents of which would also be mixed with the contents of the first chamber 12 to obtain the desired solution. As an example of this, a triple chamber bag 60 is shown in FIG. 6.

This includes a third chamber 50 that is separated from the second chamber 14 by a welded seam 52. By means of a fill tube 20, that is likewise provided here, the third chamber 50 can be filled, and by means of a connecting tube 26, its contents can be fed into the first chamber 12 for mixing with the contents of the first chamber. Otherwise, like parts are denoted by like reference numerals so that a further description can be dispensed with.

In FIG. 7 there is shown an apparatus 40 for insulating the second chamber of the multiple chamber recipient 10 during the heat sterilisation. The apparatus includes an upper portion 42 and a lower portion 44 that are connected together by a joint 46. The upper portion 42 and the lower portion 44 are each box-shaped and comprise thermal insulation 48 on their inner sides.

The multiple chamber recipient 10, that has already been described extensively with reference to FIG. 5, is laid with its first chamber 14 in the lower portion 44 of the apparatus 40. Care should be taken when doing this that the multiple chamber recipient 10 lies with the welded seam 16 on the edge of the lower portion 44. If the multiple chamber recipient 10 were to comprise several chambers requiring thermal insulation during the heat sterilisation of the multiple chamber recipient 10, these would also be arranged in the lower portion 44 of the apparatus 40.

When the apparatus 40 is closed by lowering the upper portion 42 down on the lower portion 44, the second chamber 14 of the multiple chamber recipient 10 is thermally insulated. This is shown in FIG. 8.

If the multiple chamber recipient 10 shown here is heat sterilised, for example in an autoclave, with its second chamber 14 thermally insulated by means of the apparatus 40, initially only the first chamber 12 will be heated. After the elapse of a predetermined time, the apparatus 40 will be opened by raising the upper portion 42, which can be achieved by appropriate means known to the person skilled in the art (this open condition corresponds approximately to that of the open apparatus 40 shown in FIG. 7). Hence the second chamber 14 of the multiple chamber recipient 10 will also be exposed to the sterilisation temperature and heated. In this way the hold time of the second chamber 14 at the sterilisation temperature can be intentionally controlled, as described in detail above.

List of Reference Numerals

| | |
|---|---|
| 10 | bag |
| 12 | first chamber |
| 14 | second chamber |
| 16 | welded seam |
| 18 | upper edge |
| 20 | fill tube |
| 22 | seal |
| 24 | opening |
| 26 | connecting tube |
| 28 | break-off seal |
| 30 | lower edge |
| 32 | connecting tube |
| 34 | feed tube |
| 36 | septum |
| 40 | apparatus |
| 42 | upper portion |
| 44 | lower portion |
| 46 | joint |
| 48 | thermal insulation |

-continued

| | |
|---|---|
| 50 | third chamber |
| 52 | welded seam |
| 60 | triple chamber bag |

What is claimed is:

1. A method for reducing the degradation of heat sensitive components contained in a medical substance during heat sterilization of a heat sterilizable container including a first chamber including a first amount of a first medical substance and a second chamber including a second amount of a second medical substance, said first amount being greater than said second amount, said method including heating said heat sterilizing container to a first predetermined temperature for sterilizing said first and second medical substances, thermally insulating said second chamber during at least a portion of said heating of said heat sterilizable container to said first predetermined temperature, holding said heat sterilizable container at said first predetermined temperature for a first predetermined time period, and cooling said heat sterilizable container thereafter.

2. The method of claim 1 including terminating said thermally insulating of said second chamber after a second predetermined time period following initiation of said heating of said heat sterilizable container.

3. The method of claim 2 including calculating said second predetermined time period such that after said first predetermined time period said first and second medical substances have substantially the same F-values.

4. The method of claim 1 wherein said first predetermined temperature is between 100° C. and 135° C.

5. The method of claim 4 wherein said first predetermined temperature is about 121° C.

6. The method of claim 1 wherein said first predetermined time period is greater than one minute.

7. The method of claim 6 wherein said first predetermined time period is less than 15 minutes.

8. The method of claim 1 wherein said heat sterilizable container includes a third chamber including a third amount of a third medical substance, said third amount being less than said first amount, and including thermally insulating said second and third chambers during said at least a portion of said heating of said heat sterilizable container to said first predetermined temperature.

9. The method of claim 8 wherein said thermally insulating of said second and third chambers comprises disposing said second and third chambers in a thermally insulating jacket.

10. The method of claim 9 including terminating said thermally insulating of said second and third chambers after a second predetermined time period following initiation of said heating of said heat sterilizable container by removing said thermally insulating jacket.

11. The method of claim 10 including calculating said second predetermined time period such that after said first predetermined time period said first and second medical substances have substantially the same F-values.

12. The method of claim 1 wherein said heat sterilizable container comprises a flexible bag.

13. The method of claim 12 wherein said medical substances are selected for producing a dialysis fluid for peritoneal dialysis.

14. The method of claim 12 wherein said heat sterilizable container includes a third chamber including a third amount of a third medical substance, said third amount being less than said first amount, and including thermally insulating both said second and third chambers during said at least a portion of said heating of said heat sterilizable container to said first predetermined temperature.

15. The method of claim 14 wherein said second medical substance comprises glucose at a first concentration and said third medical substance comprises glucose at a second concentration, said first concentration and said second concentration being different concentrations.

16. The method of claim 14 wherein said second medical substance comprises glucose at a first concentration and said third medical substance comprises glucose at a second concentration, said first concentration and said second concentration being substantially the same, and said second and third amounts being different amounts.

17. The method of claim 12 wherein said medical substances are selected for parenteral feeding.

18. The method of claim 1 including interrupting said heating of said heat sterilizable container at a second predetermined temperature for a second predetermined time period.

19. Apparatus for reducing the degradation of heat sensitive components contained in a medical substance during heat sterilization of a heat sterilizable container including a first chamber including a first amount of a first medical substance and a second chamber including a second amount of a second medical substance, said first amount being greater than said second amount, said apparatus comprising thermal insulation movable between a first position wherein said second chamber is substantially enclosed by said thermal insulation and a second position wherein said second chamber is at least partially free of said thermal insulation.

20. The apparatus of claim 19 wherein said thermal insulation comprises a closable container including an upper portion, a lower portion, and a joint connecting said upper portion to said lower portion.

21. The apparatus of claim 20 wherein both said upper portion and said lower portion include a portion of said thermal insulation therein.

22. The apparatus of claim 21 wherein said upper portion and said lower portion form a thermally insulating cavity for said second chamber of said heat sterilizable container.

* * * * *

UNITED STATES PATENT AND TRADEMARK OFFICE
CERTIFICATE OF CORRECTION

PATENT NO. : 6,663,829 B1
DATED : December 16, 2003
INVENTOR(S) : Per Kjellstrand It is certified that error appears in the above-identified patent and that said Letters Patent is hereby corrected as shown below:

Delete the title page, and substitute therefor the attached title page.

Delete the specification, columns 1-10 and substitute therefor the attached columns 1-12.

Signed and Sealed this

Fifteenth Day of February, 2005

JON W. DUDAS
*Director of the United States Patent and Trademark Office*

United States Patent
Kjellstrand (10) Patent No.: US 6,663,829 B1
(45) Date of Patent: Dec. 16, 2003

(54) METHOD AND APPARATUS FOR REDUCING THE DEGRADATION OF HEAT SENSITIVE COMPONENTS IN MEDICAL SUBSTANCES DURING HEAT STERILIZATION

(75) Inventor: Per Kjellstrand, Södra Sandby (SE)

(73) Assignee: Gambro AB (SE)

(*) Notice: Subject to any disclaimer, the term of this patent is extended or adjusted under 35 U.S.C. 154(b) by 0 days.

(21) Appl. No.: 09/807,036
(22) PCT Filed: Oct. 20, 1999
(86) PCT No.: PCT/SE99/01889
 § 371 (c)(1),
 (2), (4) Date: Apr. 5, 2001
(87) PCT Pub. No.: WO00/24433
 PCT Pub. Date: May 4, 2000

(30) Foreign Application Priority Data

Oct. 23, 1998 (SE) .............................. 9803627

(51) Int. Cl.⁷ .............................................. A61L 2/00
(52) U.S. Cl. .................. 422/1; 422/25; 422/40; 422/41; 422/307; 422/308; 604/28; 604/29; 604/408; 604/409; 604/410; 206/219; 206/568; 206/570
(58) Field of Search .................. 422/1, 25, 40, 422/41, 256, 307, 308; 604/28, 29, 408, 410, 409; 206/219, 568, 570

(56) References Cited

U.S. PATENT DOCUMENTS

| | | | |
|---|---|---|---|
| 4,994,057 A | * | 2/1991 | Carmen et al. ............ 604/416 |
| 4,997,083 A | * | 3/1991 | Loretti et al. ............ 206/219 |
| 5,536,469 A | * | 7/1996 | Jonsson et al. ............ 422/1 |
| 6,241,943 B1 | * | 6/2001 | Wieslander et al. ........ 422/1 |

FOREIGN PATENT DOCUMENTS

| | | |
|---|---|---|
| DE | 43 21 999 C1 | 10/1994 |
| WO | 93/09820 A1 | 5/1993 |
| WO | 97/05852 A1 | 2/1997 |

* cited by examiner

*Primary Examiner*—Krisanne Thornton
(74) *Attorney, Agent, or Firm*—Lemery David, Littenberg, Krumholz & Mentlik, LLP (57) ABSTRACT

Methods and apparatus are disclosed for reducing the degradation of heat sensitive components contained in a medical substance during heat sterilization of a heat sterilizable container including a first chamber including a first amount of a first medical substance and a second chamber including a second amount of a second medical substance, the first amount being greater than the second amount. The method includes heating the heat sterilizable container to a first predetermined temperature for sterilizing the first and second medical substances, thermally insulating the second chamber during at least a portion of the heating of the heat sterilizable container to the first predetermined temperature, holding the heat sterilizable container at the first predetermined temperature for a first predetermined time period, and cooling the heat sterilizable container thereafter.

22 Claims, 4 Drawing Sheets

METHOD AND APPARATUS FOR REDUCING THE DEGRADATION OF HEAT SENSITIVE COMPONENTS IN MEDICAL SUBSTANCES DURING HEAT STERILIZATION

FIELD OF THE INVENTION

The present invention relates to a method and apparatus for reducing the degradation of heat sensitive components in medical substances during heat sterilization, wherein the medical substances are contained in a multiple chamber container that comprises a first chamber with a first medical substance and at least one second chamber with an amount of a second medical substance that is smaller than that of the first medical substance, and the multiple chamber recipient is heated to a predetermined temperature for sterilizing the medical substances, is held at this temperature for a predetermined time period, and is subsequently cooled.

The present invention also relates to a method which can be utilised with multiple chamber containers with medical substances for parenteral feeding/nutrition, but the present method is particularly useful with multiple chamber containers that contain medical substances for generating a dialysis fluid for peritoneal dialysis.

BACKGROUND OF THE INVENTION

Currently, hemodialysis is primarily used for acute kidney failure, while for chronic kidney failure, besides transplantation, both hemodialysis and peritoneal dialysis are utilized. In the case of peritoneal dialysis, the abdominal cavity is repeatedly filled at intervals with a dialysis fluid that is then removed after a holding time. The dialysis fluid is generally a buffered ionic solution with an osmotic means, wherein glucose is primarily used as the osmotic means, and lactate is mainly used as a buffer. In this manner, urea and other substances are normally removed from the kidneys and excess water can be removed from the body. These dialysis fluids are produced in factories, transferred to plastic bags of two to five liter capacity and sterilized, in a similar manner to solutions for parenteral nutrition.

A disadvantage of these dialysis fluids is the presence of degradation products. At present, it is assumed that during heat sterilization these degradation products, and the accompanying brownish color of the fluid, are produced by the glucose. It is further presumed that some of these degradation products are responsible for bioincompatability reactions generated by the dialysis fluid. Studies confirm that the degradation products react strongly with biological tissue and have a substantial effect on the immune system and the cells of the peritoneum, either alone or in combination with lactate and/or a low pH value.

Theoretically, the dialysis fluids can be rendered sterile by filtration in place of the heatsterilization. In practice, however, this is not possible because essentially all countries stipulate that medical solutions must be sterilised by heat.

However, it is known that the degradation of glucose can be markedly reduced when the sterilization temperature is increased and the sterilization time is simultaneously shortened. It is also known that glucose degradation depends strongly on the pH value, and for example is at its lowest with a pH value between 3.0 and 3.5. However, a peritoneal dialysis fluid with such a low pH value is not permitted for the treatment of patients; for which a pH value of a little over 7 would be optimal, for example 7.1 to 7.4. As a compromise, therefore, a pH value of about 5.3 is set for conventional dialysis fluids. However, from a medical point of view, this is still too low, and is probably the cause of infusion pain in some patients. Furthermore, substantial amounts of degradation products are still generated during heat sterilization, which is undesirable for the reasons mentioned above.

An improvement is proposed in International Application No. WO 93/09820. In the dialysis fluid disclosed therein, the glucose is isolated in a small second chamber separate from the rest of the dialysis fluid located in a first chamber. The glucose is separated in this second chamber with a high concentration and a low pH value, so that the formation of degradation products of glucose during heat sterilization is substantially reduced. The pH value of the glucose in the separate second chamber is about 3.2, while the remainder of the solution in the larger chamber has a pH value of around 7. After mixing the glucose with the rest of the solution the mixture has a pH value of around 6.4, which offers an additional advantage in terms of tolerance by patients.

In International Application No. WO 97/05852, a further development of this dialysis fluid is disclosed in which the glucose is separated into two separate chambers, namely a second and third chamber, each with different concentrations. The concentrations are selected such that upon mixing the glucose from the second chamber with the rest of the solution in the first chamber, a dialysis fluid with a glucose concentration of 1.5% is obtained, upon mixing the glucose from the third chamber with the rest of the solution in the first chamber a glucose concentration of 2.5% is obtained, and upon mixing the glucose in the second and third chambers with the rest of the solution in the first chamber a glucose concentration of 4% is obtained. In this manner, the three most useful glucose concentrations can be made available with one dialysis fluid container, which offers a great advantage in terms of logistics and storage. In addition, this dialysis fluid contains low amounts of degradation products as a result of the low pH values in the second and third chambers.

Although this already represents a clear reduction in the amount of degradation products in the dialysis fluid, there are still a significant amount of degradation products present, owing to the high glucose concentration. As a result of the small quantities in the second and third chambers compared to that of the remaining solution in the first chamber, the glucose concentrations in these second and third chambers will be heated much faster during the heat sterilization than the rest of the solution in the first chamber, which contains the remaining components. This leads to the glucose in the second and third chambers being held for an unnecessary long period of time at the sterilization temperature, which results in an unnecessary increase in the degradation products. Consequently, while a considerable reduction in degradation products is achieved compared to conventional dialysis fluids, the quantity of degradation products present is nevertheless still unnecessarily high.

Finally, it is also possible to reduce the formation of degradation products during heat sterilization of multiple chamber containers by means of a two step heating procedure. In this procedure, the heating of the multiple chamber container in an autoclave is interrupted at a predetermined temperature, so that the temperatures in the first and second, and possibly the third, chamber can become essentially equal. Subsequently, the heating of the multiple chamber container proceeds to the predetermined sterilization temperature. However, it is difficult with this procedure to find the exact intermediate temperature at which no, or only few, degradation products will be formed during the holding period.

It is thus an object of the present invention to provide a method whereby the degradation of heat sensitive components in medical substances during heat sterilization is reduced, wherein the medical substances are contained in a multiple chamber container having a first chamber with a first medical substance and at least a second chamber with an amount of a second medical substance that is smaller relative to the first medical substance, and the multiple chamber recipient is heated to a predetermined temperature to sterilize the medical substances, is held at this temperature for a predetermined time, and is subsequently cooled.

SUMMARY OF THE INVENTION

In accordance with the present invention, this and other objects have now been achieved by the discovery of a method for reducing the degradation of heat sensitive components contained in a medical substance during heat sterilization of a heat sterilizable container including a first chamber including a first amount of a first medical substance and a second chamber including a second amount of a second medical substance, the first amount being greater than the second amount, the method including heating the heat sterilizable container to a first predetermined temperature for sterilizing the first and second medical substances, thermally insulating the second chamber during at least a portion of the heating of the heat sterilizable container to the first predetermined temperature, holding the heat sterilizable container at the first predetermined temperature for a first predetermined time period, and cooling the heat sterilizable container thereafter. In a preferred embodiment, the method includes terminating the thermally insulating of the second chamber after a second predetermined time period following initiation of the heating of the heat sterilizable container. Preferably, the method includes calculating the second predetermined time period such that after the first predetermined time period the first and second medical substances have substantially the same F-values.

In accordance with one embodiment of the method of the present invention, the first predetermined temperature is between 100° C. and 135° C. Preferably, the first predetermined temperature is about 121° C.

In accordance with one embodiment of the method of the present invention, the first predetermined time period is greater than one minute. Preferably, the first predetermined time period is less than 15 minutes.

In accordance with another embodiment of the method of the present invention, the heat sterilizable container includes a third chamber including a third amount of a third medical substance, the third amount being less than the first amount, and the method includes thermally insulating the second and third chambers during the at least a portion of the heating of the heat sterilizable container to the first predetermined temperature. In a preferred embodiment, the thermally insulating of the second and third chambers comprises disposing the second and third chambers in a thermally insulating jacket. In a preferred embodiment, the method includes terminating the thermally insulating of the second and third chambers after a second predetermined time period following initiation of the heating of the heat sterilizable container by removing the thermally insulating jacket.

In accordance with a preferred embodiment of the method of the present invention, the method includes calculating the second predetermined time period such that after the first predetermined time period the first and second medical substances have substantially the same F-values.

In accordance with another embodiment of the method of the present invention, the heat sterilizable container comprises a flexible bag. Preferably, the medical substances are selected for producing a dialysis fluid for peritoneal dialysis.

In accordance with one embodiment of the method of the present invention, the heat sterilizable container includes a third chamber including a third amount of a third medical substance, the third amount being less than the first amount, and the method includes thermally insulating both the second and third chambers during the at least a portion of the heating of the heat sterilizable container to the first predetermined temperature. Preferably, the second medical substance comprises glucose at a first concentration and the third medical substance comprises glucose at a second concentration, the first concentration and the second concentration being different concentrations.

In accordance with another embodiment of the method of the present invention, the second medical substance comprises glucose at a first concentration and the third medical substance comprises glucose at a second concentration, the first concentration and the second concentration being substantially the same, and the second and third amounts being different amounts.

In accordance with another embodiment of the method of the present invention, the medical substances are selected for parenteral feeding.

In accordance with another embodiment of the method of the present invention, the method includes interrupting the heating of the heat sterilizable container at a second predetermined temperature for a second predetermined time period.

In accordance with the present invention, apparatus has also been discovered for reducing the degradation of heat sensitive components contained in a medical substance during heat sterilization of a heat sterilizable container including a first chamber including a first amount of a first medical substance and a second chamber including a second amount of a second medical substance, the first amount being greater than the second amount, the apparatus comprising thermal insulation movable between a first position wherein the second chamber is substantially enclosed by the thermal insulation and a second position wherein the second chamber is at least partially free of the thermal insulation. In accordance with a preferred embodiment, the thermal insulation comprises a closable container including an upper portion, a lower portion, and a joint connecting the upper portion to the lower portion. Preferably, both the upper portion and the lower portion include a portion of the thermal insulation therein. In a preferred embodiment, the upper portion and the lower portion form a thermally insulating cavity for the second chamber of the heat sterilizable container.

In accordance with the present invention, the above objects are achieved by a second chamber with the second medical substance being thermally insulated during the heating of the multiple chambercontainer.

In this manner, a method is provided that reduces the degradation of heat sensitive components in the second chamber during heat sterilization of multiple chamber containers with different substances. The end product after mixing of the contents of the chamber thus contains substantially lower amounts of degradation products.

The second chamber can contain a quantity of a medical substance that is low relative to that in the first chamber. If this substance contains components that form degradation products when held for a long period of time at the sterilization temperature, they will thus be prevented from being heated faster and consequently remaining at the sterilization temperature longer than the substance in the first chamber. However, it is also possible that the second chamber contains the same amount of a medical substance as the first chamber, but with some of the components of this substance being very heat sensitive, so that they may be subjected to the sterilization temperature for only a shorter period of time relative to the substance in the first chamber. By means of the thermal insulation of the second chamber, heating of the second chamber can also be deliberately delayed, as a result of which the desired holding time at the sterilization temperature can be set.

The holding time of the second chamber at the sterilization temperature can advantageously be more precisely adjusted, in accordance with a preferred embodiment of the present invention, when the thermal insulation is removed at a predetermined time after commencing the heating of the multiple chamber container. In this manner, the point in time at which the second chamber of the multiple chamber container is also exposed to the heating environment can be accurately set. Furthermore, since the point in time of cooling of the multiple chamber container is also predetermined, a precisely controlled heat sterilization with a defined holding time at the sterilization temperature is also separately possible for the second chamber.

In accordance with a further preferred embodiment of the present invention, the time for removing the thermal insulation is advantageously determined such that the first and second medical substances in the first and second chambers have essentially the same F value at the end of the holding time. F is utilized here as a gauge of the capacity of a sterilization process to kill microbes, or the sterilization capacity of a sterilization process, and is predominantly utilized in the food and medical industries. It is a reference gauge and signifies a specific rate of microbes killed during a sterilization process, F representing the time required to achieve this specific death rate at 121° C.

If the first and second medical substances have essentially the same F value, then this indicates that both substances have undergone essentially the same degree of sterilization and, in particular, that the second chamber or the second substance has not been subjected to an unnecessary over-sterilization as a result of overheating. Overheating the second chamber would lead to a substantial increase in the degradation products. It is to be noted at this point that a correlation exists between the F value and the degradation in the sense that with an increasing F value, the degradation products also increase, and vice versa.

In order to achieve adequate sterilization of the multiple chambercontainer, it is advantageously heated to a temperature of between 100° C. and 135° C., preferably to a temperature of 121° C. The sterilization process is advantageously controlled such that the multiple chamber container is held for between 1 minute to several hours at this predetermined temperature, and preferably about 15 minutes.

The method for reducing the degradation of heat sensitive components in medical substances described herein is not limited only to multiple chamber containers with two chambers, but may also be applied to multiple chamber containers with more than two chambers. Therefore, according to another preferred embodiment of the present invention, the method is utilized for a multiple chamber container that also includes a third chamber with an amount of a third medical substance that is smaller relative to that of the first medical substance, the third chamber being thermally insulated together with the second chamber during heating of the multiple chambercontainer. In this case, once again, the second chamber with the second medical substance and the third chamber with the third medical substance are advantageously arranged in a thermally insulating jacket, that is opened a predetermined time after commencing heating of the multiple chamber container. The second chamber and the third chamber can contain different amounts of the same substance, or the same amount of different substances.

The time at which the thermal insulation is removed is likewise advantageously defined such that the first, second and third medical substances in the first, second and third chambers have essentially the same F value at the end of the holding time. If the second and third chambers contain different amounts of a medical substance, the F value of the largest amount determines the removal of the thermal insulation. This should be essentially the same as the F value in the first chamber. The F value of the smaller amount in the other chamber will then be somewhat higher; this deviation from the desired F value has to be accepted in view of the required sterilization of the larger amount. However, in order to again achieve a nearly equivalent F value in this case, the insulation can be formed differently in different areas. For example, it could be formed thinner in the area of the second or third chamber, when these contain a larger amount, so that the sterilizing heat reaches the large amount before removal of the insulation, and is able to heat this to a small degree. On the other hand, the second and third chambers will be respectively insulated such that the insulation of each can be successively removed independently of one another.

The thermally insulating jacket may take any desired form. For example, it can consist of an insulating material which, upon reaching a predetermined temperature will collapse or shrink, thus allowing the elevated surrounding temperature to reach the multiple chamber container. In this manner, heating of the second and possibly also the third chamber will be delayed, and as a result, the time during which the second, and possibly the third, chamber is held at the sterilization temperature can be controlled.

Another possibility for a thermally insulating jacket is a container with thermally insulating walls. The second, and possibly the third, chamber would be laid in this container with the first chamber remaining outside, and the container would be closed. In this manner, the second, and possibly the third, chamber will be thermally insulated, so that initially only the first chamber is heated. When the predetermined point of time is reached, the container is opened and the second chamber, and possibly third chamber, will be exposed to the sterilizing heat and heated to the same temperature as the first chamber. In this way, the holding time of the second, and possibly third, chambers can be precisely determined independently of that of the first chamber. When the predetermined holding time of the first chamber is terminated, the multiple chamber container is cooled down. During this procedure, care should be taken that cooling occurs rapidly, so that degradation products are not formed unnecessarily as a result of slow cooling.

The method of the present invention can be applied to multiple chamber containers of any desired form, however it is preferably utilized with a multiple chamber container formed as a flexible bag. The method of the present invention can likewise be applied to multiple chamber containers that hold any desired medical substance. For example, the multiple chamber container may hold substances for parenteral feeding. Also, the substances can take any desired form. For example, the medical substances can be solutions in liquid form, they can also be concentrates in powder form. However, the method of the present invention is preferably applied to multiple chamber bags containing medical substances for the production of a dialysis fluid for peritoneal dialysis. According to a preferred embodiment of the present invention, the second medical substance and the third medical substance in the second and third chambers, respectively, comprise different concentrations of glucose, which is required for the dialysis fluid, or, according to another preferred embodiment of the present invention, the same concentration of glucose in different quantities.

BRIEF DESCRIPTION OF THE DRAWINGS

Examples of the method according to the present invention are provided by way of illustration in the accompanying drawings. The figures contained therein show the temperature curve and the F curve and thus the degradation, on the one hand, for the sterilization of a double chamber bag according to conventional heat sterilization in an autoclave, and on the other hand, for the heat sterilization of a double chamber bag in an autoclave with the method according to the present invention. Therein, the F value "$F_o$" is the F value corresponding to a sterilization temperature of 121° C. The drawings discussed in the following detailed description thus include.

DETAILED DESCRIPTION

Referring to the Figures, FIG. 1 shows the temperature curve of a double chamber bag during conventional heat sterilization in an autoclave, wherein the dashed line 1 shows the temperature curve in the second chamber, and the continuous line 3 shows the temperature curve in the first chamber. The second chamber contains a smaller quantity of medical substance compared to that of the first chamber. Therefore, the contents of the second chamber will be heated faster during heating of the multiple chamber bag, as can be clearly seen from the temperature curve (line 1) in the second chamber during the first ten minutes. The second chamber reaches the sterilization temperature, which here is about 121° C., much faster, and is also held there substantially longer than the first chamber. The first chamber requires a longer period for heating owing to the larger quantity of medical substance therein, as is evident from the temperature curve (line 3) during the first ten minutes. The first chamber reaches the sterilization temperature much later, and is also held at this sterilization temperature for a shorter period (line 3). After reaching the end of the predetermined holding time at the sterilization temperature for the multiple chamber container or for the first chamber, the multiple chamber container is cooled down. During this time period, the second chamber, or the contents of the second chamber, cools faster (line 1) owing to the smaller quantity of medical substance therein relative to that of the first chamber (line 3). The longer holding time of the second chamber at the sterilization temperature causes a higher formation of degradation products and also leads to an elevated F value in the second chamber, which is superfluous in terms of sterilization.

This is shown in FIG. 2. FIG. 2 shows the $F_o$ curve during heat sterilization according to FIG. 1. As can be clearly seen therein, in the second chamber (line 1) an $F_o$ value is obtained which is almost double that in chamber 1 (line 3). The $F_o$ value of about ten obtained in chamber 1 is normally a sufficient $F_o$ value for sterilization, while the $F_o$ value obtained in the second chamber of around twenty is unnecessarily high.

To avoid this over-sterilization and the accompanying increased degradation of, for example, glucose contained in the second chamber, the second chamber is provided with a thermally insulating jacket, which is removed a predetermined time after the beginning of the heating process. The resulting temperature curve during heat sterilization is shown in FIG. 3. It can thus be clearly seen that the beginning of the heating of the second chamber (line 2) is markedly delayed compared to the beginning of the heating of the first chamber (line 3). After about twenty minutes, the thermally insulating jacket of the second chamber is removed, so that the second chamber is likewise heated rapidly to the sterilization temperature, together with the first chamber. After a predetermined holding time of the multiple chamber container at the sterilization temperature, the multiple chamber container is cooled, as is apparent from the continuing temperature curve of the first and second chambers (line 3, line 1).

In contrast to the heat sterilization of the multiple chamber container without the thermal insulation of the second chamber according to FIG. 1, the second chamber in this case remains at the sterilization temperature essentially as long as the first chamber. In this way, on the one hand, the excessive and unnecessary formation of degradation products is prevented and, on the other, an over-sterilization of the medical substance contained in the second chamber is avoided.

This is shown in FIG. 4. FIG. 4 shows the $F_o$ curve during the heat sterilization according to FIG. 3. Because the first and second chambers, or their contents, are held for essentially the same time at the sterilization temperature, the result is an almost identical $F_o$ value. The $F_o$ value of the medical substance in the second chamber (line 1) differs only slightly from the $F_o$ value of the substance in the first chamber (line 3). Due to the later commencement of heating, and the slightly higher temperature relative to that of the first chamber during the holding time, the $F_o$, temperature curve of the second chamber (line 1) lies slightly below the $F_o$ temperature curve of the first chamber (line 3) at the beginning, but then lies slightly above it at the end of the sterilization. However, over-sterilization of the second chamber has not occurred, nor were excessive degradation products formed in the second chamber during the sterilization.

The method performed in this example on a two chamber bag can also be applied to three or multiple chamber bags, as described in detail above. In this case, the larger first chamber, or the first chamber filled with the larger amount of medical substance, determines the holding time of the multiple chamber bag in the autoclave, while the chamber of the second, and possibly third, fourth, etc. chambers provided with a thermally insulating jacket that includes the largest amount of medical substance, determines the time of removal of the thermally insulating jacket. The desired, lowest required F value, that corresponds to an adequate sterilization, is always to be selected as a gauge for the holding time of the multiple chamber container in the autoclave, or for the removal of the thermal insulation.

In FIG. 5 a double chamber bag 10 is shown, that is to be sterilized according to the method of the present invention. The multiple chamber bag 10 includes a first larger chamber 12 and a second smaller chamber 14. In the present case, the multiple chamber container 10 contains a dialysis solution for peritoneal dialysis and includes an electrolytic solution in the first chamber 12 and a glucose solution in the second chamber 14.

The first chamber 12 is separated from the second chamber 14 by a welded seam 16, in which there is arranged a connecting tube 26. The connecting tube 26 is closed at one end by a break-off seal 28. A fill tube 20, through which the second chamber 14 is filled, is connected at the upper edge 18 of the multiple chamber container 10. The outer end of the fill tube 20 is provided with a seal 22 which may be achieved simply by melting the end of the fill tube 20, for example. Moreover, at the upper edge 18 there is provided an opening 24, by which the multiple recipient bag 10 can be suspended. At the lower edge 30 of the multiple chamber recipient 10, there is arranged a connection tube 32, by means of which the contents of the first chamber 12 can be supplied to a patient. Furthermore, there is also provided a fill tube 20 at the lower edge 30, through which the first chamber 12 is filled. This fill tube 20 is also provided with a seal 22 at its outer end. Finally, a feed tube 34 is also arranged at the lower edge 30, by means of which medication can be supplied to the contents of the first chamber 12, for example. The feed tube 34 is closed at its outer end with a septum 36, so that the injection of medication into the first chamber 12 is possible. Before the dialysis solution is administered to the patient, the contents of the first chamber 12 and second chamber 14 are mixed together. To this end, the break-off seal 28 is broken off so that the connecting tube 26 between the first chamber 12 and the second chamber 14 is opened. The contents of the second chamber 14 then run through the connecting tube 26 into the first chamber 12, and mix with the solution located therein. Subsequently, the mixed solution can be supplied to the patient through the connecting tube 32.

It is again to be noted at this point that the multiple chamber container 10 can also include a third, or even more chambers, the contents of which would also be mixed with the contents of the first chamber 12 to obtain the desired solution. As an example of this, a triple chamber bag 60 is shown in FIG. 6. This includes a third chamber 50 that is separated from the second chamber 14 by a welded seam 52. By means of a fill tube 20, that is similarly provided in this case, the third chamber 50 can be filled, and by means of a connecting tube 26, its contents can be fed into the first chamber 12 for mixing with the contents of the first chamber. Otherwise, like parts are denoted by like reference numerals so that a further description is not necessary.

In FIG. 7 there is shown apparatus 40 for insulating the second chamber of the multiple chamber container 10 during heat sterilization. The apparatus includes an upper portion 42 and a lower portion 44 that are connected together by a joint 46. The upper portion 42 and the lower portion 44 are each box-shaped and comprise thermal insulation 48 on their inner sides.

The multiple chamber container 10, that has already been described extensively with reference to FIG. 5, is laid with its first chamber 14 in the lower portion 44 of the apparatus 40. Care should be taken when doing so that the multiple chamber container 10 lies with the welded seam 16 on the edge of the lower portion 44. If the multiple chamber container 10 were to comprise several chambers requiring thermal insulation during heat sterilization of the multiple chamber container 10, these would also be arranged in the lower portion 44 of the apparatus 40.

When the apparatus 40 is closed by lowering the upper portion 42 down on the lower portion 44, the second chamber 14 of the multiple chamber container 10 is thermally insulated. This is shown in FIG. 8.

If the multiple chamber container 10 shown here is heat sterilized, for example in an autoclave, with its second chamber 14 thermally insulated by means of the apparatus 40, initially only the first chamber 12 will be heated. After elapse of a predetermined time, the apparatus 40 will be opened by raising the upper portion 42, which can be achieved by appropriate means known to a person skilled in the art (this open condition corresponds approximately to that of the open apparatus 40 shown in FIG. 7). Hence the second chamber 14 of the multiple chamber container 10 will also be exposed to the sterilization temperature and heated. In this way the holding time of the second chamber 14 at the sterilization temperature can be intentionally controlled, as described in detail above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for reducing the degradation of heat sensitive components contained in a medical substance during heat sterilization of a heat sterilizable container including a first chamber including a first amount of a first medical substance and a second chamber including a second amount of a second medical substance, said first amount being greater than said second amount, said method including heating said heat sterilizable container to a first predetermined temperature for sterilizing said first and second medical substances, thermally insulating said second chamber during at least a portion of said heating of said heat sterilizable container to said first predetermined temperature, holding said heat sterilizable container at said first predetermined temperature for a first predetermined time period, and cooling said heat sterilizable container thereafter.

2. The method of claim 1 including terminating said thermally insulating of said second chamber after a second predetermined time period following initiation of said heating of said heat sterilizable container.

3. The method of claim 2 including calculating said second predetermined time period such that after said first predetermined time period said first and second medical substances have substantially the same F-values.

4. The method of claim 1 wherein said first predetermined temperature is between 100° C. and 135° C.

5. The method of claim 4 wherein said first predetermined temperature is about 121° C.

6. The method of claim 1 wherein said first predetermined time period is greater than one minute.

7. The method of claim 6 wherein said first predetermined time period is less than 15 minutes.

8. The method of claim 1 wherein said heat sterilizable container includes a third chamber including a third amount of a third medical substance, said third amount being less than said first amount, and including thermally insulating said second and third chambers during said at least a portion of said heating of said heat sterilizable container to said first predetermined temperature.

9. The method of claim 8 wherein said thermally insulating of said second and third chambers comprises disposing said second and third chambers in a thermally insulating jacket.

10. The method of claim 9 including terminating said thermally insulating of said second and third chambers after a second predetermined time period following initiation of said heating of said heat sterilizable container by removing said thermally insulating jacket.

11. The method of claim 10 including calculating said second predetermined time period such that after said first predetermined time period said first and second medical substances have substantially the same F-values.

12. The method of claim 1 wherein said heat sterilizable container comprises a flexible bag.

13. The method of claim 12 wherein said medical substances are selected for producing a dialysis fluid for peritoneal dialysis.

14. The method of claim 12 wherein said heat sterilizable container includes a third chamber including a third amount of a third medical substance, said third amount being less than said first amount, and including thermally insulating both said second and third chambers during said at least a portion of said heating of said heat sterilizable container to said first predetermined temperature.

15. The method of claim 14 wherein said second medical substance comprises glucose at a first concentration and said third medical substance comprises glucose at a second concentration, said first concentration and said second concentration being different concentrations.

16. The method of claim 14 wherein said second medical substance comprises glucose at a first concentration and said third medical substance comprises glucose at a second concentration, said first concentration and said second concentration being substantially the same, and said second and third amounts being different amounts.

17. The method of claim 12 wherein said medical substances are selected for parenteral feeding.

18. The method of claim 1 including interrupting said heating of said heat sterilizable container at a second predetermined temperature for a second predetermined time period.

19. Apparatus for reducing the degradation of heat sensitive components contained in a medical substance during heat sterilization of a heat sterilizable container including a first chamber including a first amount of a first medical substance and a second chamber including a second amount of a second medical substance, said first amount being greater than said second amount, said apparatus comprising thermal insulation movable between a first position wherein said second chamber is substantially enclosed by said thermal insulation and a second position wherein said second chamber is at least partially free of said thermal insulation.

20. The apparatus of claim 19 wherein said thermal insulation comprises a closable container including an upper portion, a lower portion, and a joint connecting said upper portion to said lower portion.

21. The apparatus of claim 20 wherein both said upper portion and said lower portion include a portion of said thermal insulation therein.

22. The apparatus of claim 21 wherein said upper portion and said lower portion form a thermally insulating cavity for said second chamber of said heat sterilizable container.

* * * * *